United States Patent [19]

Islam

[11] Patent Number: 6,133,254
[45] Date of Patent: Oct. 17, 2000

[54] USE OF ASPIROCHLORINE OR DERIVATIVES THEREOF AS IMMUNOSUPPRESSIVE AGENTS

[75] Inventor: Khalid Islam, Como, Italy

[73] Assignee: Gruppo Lepetit, S.p.A., Milan, Italy

[21] Appl. No.: 09/171,848

[22] PCT Filed: Apr. 23, 1997

[86] PCT No.: PCT/EP97/02049

§ 371 Date: Oct. 26, 1999

§ 102(e) Date: Oct. 26, 1998

[87] PCT Pub. No.: WO97/41862

PCT Pub. Date: Nov. 13, 1997

[30] Foreign Application Priority Data

May 3, 1996 [EP] European Pat. Off. .............. 96106991

[51] Int. Cl.[7] .......................... A61K 31/545; A61K 31/55
[52] U.S. Cl. .................. 514/211.04; 514/206; 514/208; 514/213; 514/215
[58] Field of Search ..................... 514/206, 208, 514/211.04, 213, 215

[56] References Cited

U.S. PATENT DOCUMENTS 3,991,052  11/1976  Berg et al. .......................... 260/243 R
4,001,086   1/1977  Berg et al. .............................. 195/81

OTHER PUBLICATIONS

Patent Abstract of Japan, vol. 96, No. 12 Dec. 26, 1996.

Chemical Abstracts, vol. 113, No. 11, Sep. 10, 1990, Columbus, Ohio Abstract No. 94510t G.F. Gause et al.

*Primary Examiner*—Theodore J. Criares
*Attorney, Agent, or Firm*—Balaram Gupta

[57] ABSTRACT

Use of a compound of formula (I) wherein R represents hydrogen or chlorine, for preparing an immunosuppressive medicament.

7 Claims, No Drawings

USE OF ASPIROCHLORINE OR DERIVATIVES THEREOF AS IMMUNOSUPPRESSIVE AGENTS

The present invention refers to a new therapeutic use as immunosuppressive agent of a compound of formula I

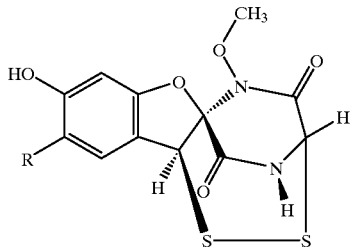

wherein R represents hydrogen or chlorine.

As known, immunity is concerned with the recognition and disposal of foreign antigenic material which is present in the body. Typically the antigens are in the form of particulate matters (i.e., cells, bacteria, etc.) or large proteins or polysaccharide molecules which are recognized by the immune system as being "non-self", i.e., detectably different from or foreign to the animal's own constituents. Potential antigens can be a variety of substances, often proteins, which are most frequently located on the outer surfaces of cells. For example, potential antigens can be found on pollen grains, tissue grafts, animal parasites, viruses, and bacteria. Once the antigenic material is recognized as "non-self" by the immune system, natural (non-specific) and/or adaptive immune responses can be initiated and maintained by the action of specific immune cells, antibodies and the complement system. Under certain conditions or disease states, an animal's immune system may recognize its own constituents as "non-self" and initiate an immune response against "self" material.

An immune response can be carried out by the immune system by means of natural or adaptive mechanisms, each of which are composed of both cell-mediated and humoral elements. Natural mechanisms for immune response refer to those mechanisms involved in essentially non-specific immune reactions which involve the complement system and myeloid cells, such as macrophages, mast cells and polymorphonuclear leukocytes (PMN), in reacting to certain bacteria, viruses, tissue damage and other antigens. These natural mechanisms provide what is referred to as natural immunity. Adaptive mechanisms for immune response refer to those mechanisms which are mediated by lymphocytes (T and B cells) and antibodies which can respond selectively to thousands of different materials recognized as "non-self". These adaptive mechanisms provide what is referred to as adaptive immunity and lead to a specific memory and a permanently altered pattern of response in adaptation to the animal's own environment. Adaptive immunity can be provided by the lymphocytes and antibodies separately or, more commonly, can be provided by the interaction of lymphocytes and antibodies with the complement system and myeloid cells of the natural mechanisms of immunity. The antibodies provide the humoral element of the adaptive immune response and the T-cells provide the cell-mediated element of the adaptive immune response.

More particular by adaptive mechanisms of immune response involve the actions against specific antigens of antibody secreted by B-lymphocytes (or B-cells) as well as the actions of various T-lymphocytes (or T-cells) on a specific antigen, on B-cells, on other T-cells or on macrophages.

The cell-mediated immune response is controlled and monitored by the T-cells through a variety of regulatory messenger compounds secreted by the myeloid cells and the lymphocyte cells. Through the secretion of these regulatory messenger compounds, the T-cells can regulate the proliferation and activation of other immune cells such as B-cells, macrophages, PMN and other T-cells. For example, upon binding a foreign antigen, a macrophage or other antigen presenting cell can secrete interleukin-1 (IL-1) which activates the Helper T-cells. T-cells in turn secrete certain lymphokines, including interleukin-2 (IL-2) and γ-interferon, each of which have a variety of regulatory effects in the cell-mediated immune response.

The ability of the immune system, and in particular the cell-mediated immune system, to discriminate between "self" and "non-self" antigens is vital to the functioning of the immune system as a specific defense against invading microorganisms. "Non-self" antigens are those antigens on substances in the body which are detectably different (or from foreign to) the animals own constituents and "self" antigens are those antigens which are not detectably different (or from foreign to) the animals own constituents. Although the immune response is a major defense against foreign substances which can cause a disease, it cannot distinguish between helpful and harmful foreign substances and destroys both.

There are certain situations, such as with an allogeneic transplant or in the "graft versus host" diseases, where it would be extremely useful to suppress the immune response in order to prevent the rejection of helpful foreign tissue or organs. Allogeneic tissues and organs are tissues and organs from a genetically different member of the same species. A "graft versus host" disease occurs where the transplanted tissue, for example in a bone marrow transplant, contains allogeneic T-cells of the donor which cause an immune response against the recipient's own tissues. Although both humoral and cell-mediated immune responses play a role in the rejection of allogeneic tissues and organs, the primary mechanism involved is the cell-mediated immune response. Suppression of the immune response, and in particular, suppression of cell-mediated immune response, would thus be useful in preventing such rejection of allograft tissues and organs. For example, cyclosporin A is currently used as an immunosuppressive agent in the treatment of patients receiving allogeneic transplants and in "graft versus host" disease.

There are times when the individual's immunological response causes more damage or discomfort than the invading microbes or foreign material, as in the case of allergic reactions. Suppression of the immune response in these cases would be desirable.

Occasionally, the immunological mechanisms become sensitized to some part of the individual's own body causing interference with or even destruction of that part. The ability to distinguish between "self" and "not-self" is impaired and the body begins to destroy itself. This can result in autoimmune diseases such as rheumatoid arthritis, insulin-dependent diabetes mellitus (which involves the autoimmune destruction of the β-cells of the islets of Langerhans which are responsible for the secretion of insulin), certain hemolytic anemias, rheumatic fever, thyroiditis, ulcerative colitis, myasthenia gravis, glomerulonephritis, allergic encephalomyelitis, continuing nerve and liver destruction which sometimes follows viral hepatitis, multiple sclerosis and systemic lupus erythematosus. Some forms of autoimmunity come about as the result of trauma to an area usually not exposed to lymphocytes such as neural tissue of the lens of the eye. When the tissues in these areas become exposed to lymphocytes, their surface proteins can act as antigens and trigger the production of antibodies and cellular immune responses which then begin to destroy those tissues. Other autoimmune diseases develop after exposure to antigens which are antigenically similar to, and that therefore cross-react with, the individual's own tissue. Rheumatic fever is an example of this type of diseases in which the antigen of the streptococcal bacterium which causes rheumatic fever is cross-reactive with parts of the human heart. The antibodies cannot differentiate between the bacterial antigens and the heart muscle antigens and cells so that either of those antigens can be destroyed by their action. Suppression of the immune system in these autoimmune diseases would be useful in minimizing or eliminating the effects of the disease. Certain of these autoimmune diseases, for example, insulin-dependent diabetes mellitus, multiple sclerosis and rheumatoid arthritis, are characterized as being the result of a cell-mediated autoimmune response and appear to be due to the action of T-cells [see Sinha et al, *Science* 248, 1380 (1990)].

Suppression of the immune response would thus be useful in the treatment of patients suffering from autoimmune diseases. More particularly, suppression of cell-mediated immune response would be useful in the treatment of patients suffering from autoimmune diseases due to the action of T-cells such as insulin-dependent diabetes mellitus, multiple sclerosis and rheumatoid arthritis.

The compound represented by the above formula I wherein R is chlorine is known as aspirochlorine.

This compound is disclosed in U.S. Pat. No. 3,991,052 as antibiotic A-30641; as disclosed therein, said compound is the main component of a complex obtained by fermenting the microbial strain *Aspergillus tamarii* NRRL 8101, under submerged aerobic conditions. U.S. Pat. 3,991,052 discloses an antifungal activity for this compound.

Aspirochlorine turned out to be (see K. Sakata et al., Agric. Biol. Chem., 47(8), 1983, pp. 2673–2674) the true antimicrobial constitutent of an antifungal antibiotic originally named "oryzachlorin", disclosed by A. Kato et al., Jour. Antib., 1969, 22, pp. 322–326. Said substance was isolated from the fermentation broths of *Aspergillus oryzae* IAM-2613 and its activity against the growth of *Candida albicans* was reported; in said article, also indications about its antiviral and antitumor activity were also given.

The antifungal properties of aspirochlorine (reported as A30641) were confirmed by D. H. Berg et al, Jour. Antib., 1976, 29, pp. 394–397; in said article, the authors also report that A30641 has only a marginal antiviral activity.

All the above mentioned literature report an incorrect structure for aspirochlorine. The correct structure (as shown in formula I) has been assigned only later on, by K. Sakata et al., Tetr. Lett., 28, 46 (1987), pp. 5607–5610.

In addition to the above mentioned microbial fermentation processes, a chemical process for the synthesis of aspirochlorine has been recently disclosed by G. F. Miknis et al., J. Am. Soc., 1993, 115, pp. 536–547.

The compound of formula I wherein R is hydrogen (de-chloro aspirochlorine) has been described by K. Sakata et al., Tennen Yuki Kagobutsu Toronkai Koen Yoshishu (1987), 29, 684–91 (See also Chem. Abstract, 108, 128151). Said compound is produced by modifying the halogen sources of the fermentation medium of *A. orizae* and shows also an antifungal activity similar to that of aspirochlorine.

It has now been found that the compounds of formula I possess an immunosuppressive activity.

The immunosuppressive activity of the compounds of the invention may be demonstrated by standard immunological tests, wherein the expression of IL-2 receptors (IL-2R) is induced with Concanavalin A (Con A) in primary human T-cells and the immunosuppressive activity is given as percentage inhibition of the IL-2 receptors expression.

For aspirochlorine an $IC_{50}$ value lower than 0.1 μg/ml has been determined, while for de-chloro aspirochlorine said value is slightly higher than 0.1 μg/ml.

In view of the above activity, the compounds of formula I may be employed for the preparation of immunosuppressive medicaments, in particular for suppressing cell-mediated immunity.

Immunosuppressive pharmaceutical compositions containing the compound of formula I would thus be particularly useful for treating those diseases connected with an altered immunologic adaptive response, such as autoimmune diseases, allergic reactions and "graft versus host" disease, as reported above. Such formulation would be particularly effective for preventing or inhibiting further deterioration or worsening of the conditions of a patient suffering from those diseases. Said immunosuppressive pharmaceutical compositions would also be useful in a prophylactic treatment of patients who received or are going to receive an allogeneic tissue or organ transplant, for preventing undesired immunologic reactions.

As used herein, the term "patient" refers to a warm-blooded animal such as a mammal which suffers from a disease, such as an autoimmune disease or "graft versus host" disease, or is in danger of rejection of a transplanted allogeneic tissue or organ. It is understood that humans, pet animals, mice and rats are included within the scope of the term "patient".

Based on standard clinical and laboratory tests and procedures, an attending diagnostician, as a person skilled in the art, can readily identify those patients who are in need of the treatment with an immunosuppressive agent such as a compound of formula I.

An effective immunosuppressive amount of a compound of formula I is that amount which is effective, upon single or multiple dose administration to a patient, in providing an immunosuppressive effect or, more particularly, a cell-mediated immunosuppressive effect. An immunosuppressive effect refers to the slowing, interrupting, inhibiting or preventing the further expression of the immune response or of the cell-mediated immune response.

An effective immunosuppressive amount of a compound of formula I can be readily determined by the attending diagnostician, as one skilled in the art, by the use of known techniques and by observing results obtained under analogous circumstances. In determining the effective amount or dose, a number factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

An effective immunosuppressive amount of a compound of formula (1) is expected to vary from about 0.1 milligram per kilogram of body weight per day (mg/kg/day) to about 100 mg/kg/day. Preferred amounts are expected to vary from about 0.5 to about 10 mg/kg/day.

A pharmaceutical composition comprising a compound of formula I can be administered in any form or mode which makes the compound bioavailable in effective amounts, including oral and parenteral routes. For example, it can be administered orally, subcutaneously, intramuscularly, intravenously, transdermally, intranasally, rectally, and the like. Oral administration is generally preferred. One skilled in the art of preparing formulations can readily select the proper form and mode of administration depending upon the particular characteristics of the compound selected, the disease state to be treated, the stage of disease, and other relevant circumstances.

The compounds can be administered in the form of a pharmaceutical composition in combination with pharmaceutically acceptable carriers or excipients, the proportion and nature of which are determined by the solubility and chemical properties of the compound selected, the chosen route of administration, and standard pharmaceutical practice.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solutions, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0–300 milligrams of a compound of the invention.

The tablets, pills, capsules, troches and the like may also contain one or more of the following adjuvants: binders such as microcrystalline cellulose, gum tragacanth or gelatin; excipients such as starch or lactose; disintegrating agents such as alginic acid, Primogel™, corn starch and the like; lubricants such as magnesium stearate or Sterotex™; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of formula I may be incorporated into a solution or suspension. These preparations should contain at least 0.1% of a compound of the invention, but may be varied to be between 0.1 and about 50% of the weight thereof. The amount of the compound present in such compositions should be such that a suitable dosage will be obtained. Preferred compositions and preparations are prepared so that a parenteral dosage unit contains between 5.0 to 100 milligrams of the compound of formula I.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

For determining the immunosuppressive activity of the compounds of formula I, the following protocol may be employed, wherein the expression of IL-2 receptors (IL-2R) is induced with Concanavalin A (Con A) in primary human T-cells. The immunosuppressive activity of the compounds of formula I is then given as percentage inhibition of the IL-2R expression in the T-cells.

1) T-cell Preparation

Human peripheral blood lymphocytes (PBLs) are isolated from a 200 ml sample of blood (in 0.01% M sodium citrate) using Histo-Paque-1077 (Sigma). The blood is diluted 1:1 with Hanks' Balanced Salt Solution (Sigma) and 10 ml of the diluted blood is layered over 10 ml Histo-Paque-1077 in 50 ml tubes (Falcon, Polypropylene). Hanks' solution and Histo-Paque should be at room temperature. Tubes are centrifuged at room temperature for 30 minutes at 1400 RPM. Plasma is removed and the cells recovered at the interface are washed in Dulbecco's Phosphate Buffered Saline (Gibco BRL, DPBS), centrifuged 5 minutes at 1400 RPM and washed again with DPBS. The cells are counted and resuspended at $2 \times 10^6$ cells/ml in RPMI 1640 (Gibco BRL). 2 ml of cell solution are placed in each well of a 6 well plate (Falcon, Tissue Culture Grade). The plates are incubated at 37°C. for 2 h. After incubation, the supernatant is removed and saved. The adherant macrophage layer is washed 2 times with DPBS and the plate tapped to remove the nonadherant cells settled on this layer. The supernatant and washings are combined, centrifuged, counted and resuspended at $2.0 \times 10^6$ cells/ml in RPMI 1640 with 10% Fetal Calf Serum (Hyclone, FCS), $5 \times 10^{-5}$ M 2-Mercaptoethanol (Sigma, 2-ME), 2 mM L-glutamine (Gibco BRL), 100 U/ml penicillin (Gibco BRL), 100 U/ml streptomycin (Gibco BRL), and 1 mM HEPES buffer (Research Organics).

2) Cell Culture

Human T-cells are cultured in 24 well plates (Falcon, Tissue Culture Grade) in a volume of 2 ml/well. Controls are without Con A (0% IL-2R expression) and with 2.5 µg/ml Con A (Sigma) (100% IL-2R expression). The compounds of the invention are tested in the following concentration 0.01, 0.1, 1.0 and 10.0 µg/ml adding a 20 µl DMSO solution at the relevant concentration (1, 10, 100 and 1000 µg/ml) to each well; 20 µl DMSO are added to groups without the tested compounds, so all groups contain the same amount of DMSO.

The plates are incubated at 37°C. for 96 h in 5% $CO_2$. Cells are harvested and wells rinsed 2 times with RPMI using vigorous pipetting. Cells are centrifuged at 1400 RPM for 5 minutes.

3) Staining for IL-2 Receptor (IL-2R)

The supernatant is removed and pellets are resuspended in 100 μl DPBS. The control sample is divided into two samples, one stained with 10 μl of a fluorescein-labeled Mouse IgG1 (isotypic control). The remaining cells are stained with 10 μl of a fluorescein-labeled anti-IL-2R (Coulter). Incubated 30 minutes at 4°C. Add 1 ml of DPBS and centrifuge 5 minutes at 1400 RPM to wash off excess antibody. Resuspended in 0.5 ml of DPBS and keep at 4° C. until flow cytometry analysis.

4) Flow Cytometry Analysis

Analysis is performed on a Coulter ELITE flow cytometer with 488 nm laser. The positive cell cursor is set with the isotypic control. A minimum of $10^4$ cells is analyzed for each sample. Histogram data is analyzed using Coulter Multigraph software.

The results are given as percentage of IL-2R expressed from T-cells in the presence of increasing amounts of immunosuppressive activity with respect to the expression of the T-cells with only the Con A activator (100% of expression), as reported in the following table I:

TABLE 1

Inhibition of IL-2R expression

| COMPOUND | Concentration (μg/ml) | % IL-2R expression |
|---|---|---|
| aspirochlorine | 0.01 | 93.5 |
| | 0.1 | 34.8 |
| | 1.0 | 23.6 |
| de-chloro aspirochlorine | 0.01 | 90.5 |
| | 0.1 | 55.8 |
| | 1.0 | 28.8 |

What is claimed is:

1. A method of treating a disease connected with an immune response comprising a step of administering to a patient in need thereof an effective immunosuppressive amount of a compound of Formula:

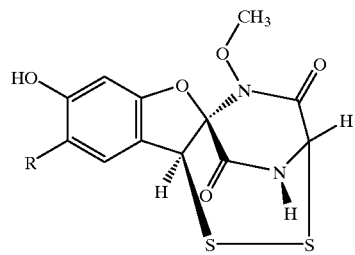

wherein R represents hydrogen or chlorine.

2. The method according to claim 1 wherein the immune response is a cell-mediated immunity.

3. The method according to claim 1 wherein the disease connected with the immune response is an allografic rejection.

4. The method according to claim 1 wherein the disease connected with the immune response is an autoimmune disease.

5. The method according to claim 4 wherein the autoimmune disease is insulin-dependent diabetes mellitus.

6. The method according to claim 4 wherein the autoimmune disease is multiple sclerosis.

7. The method according to claim 4 wherein the autoimmune disease is rheumatoid arthritis.

* * * * *